US006294564B1

(12) United States Patent
Bär

(10) Patent No.: US 6,294,564 B1
(45) Date of Patent: Sep. 25, 2001

(54) BENZIMIDAZOLES AND BENZOXAZOLES

(75) Inventor: Thomas Bär, Reichenau (DE)

(73) Assignee: Byk Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/673,650

(22) PCT Filed: Apr. 29, 1999

(86) PCT No.: PCT/EP99/02900

§ 371 Date: Nov. 1, 2000

§ 102(e) Date: Nov. 1, 2000

(87) PCT Pub. No.: WO99/57115

PCT Pub. Date: Nov. 11, 1999

(30) Foreign Application Priority Data

May 5, 1998 (EP) .................................................. 98108125

(51) Int. Cl.⁷ ...................... A61K 31/415; A61K 31/421; C07D 235/04; C07D 265/30
(52) U.S. Cl. .................... 514/394; 548/218; 548/305.1; 548/394; 514/375; 514/232.5; 544/178
(58) Field of Search .................................. 514/394, 375; 548/301.1, 305.1, 218

(56) References Cited

U.S. PATENT DOCUMENTS

| 5,665,737 | 9/1997 | Cavalla et al. | 514/338 |
| 5,814,651 | 9/1998 | Duplantier et al. | 514/394 |
| 5,889,014 | 3/1999 | Cavalla et al. | 514/269 |
| 5,998,428 | * 12/1999 | Barnette et al. | 514/285 |
| 6,121,274 | 9/2000 | Ulrich et al. | 514/278 |
| 6,172,074 | 1/2001 | Bär et al. | 514/278 |

FOREIGN PATENT DOCUMENTS

| 94/12461 | 6/1994 | (WO) . |
| 96/03399 | 2/1996 | (WO) . |
| 96/11917 | 4/1996 | (WO) . |

OTHER PUBLICATIONS

Theodore J. Torphy, George P. Livi and Siegfried B. Christensen "Novel Phosphodiesterase Inhibitors for the Therapy of Asthma" DN & P 6 (4), pp. 203–214, May 1993.*

M. A. Giembycz and G. Dent, Cliniacl and Experimental Allergy, 1992, vol. 22, pp. 337–344.*

* cited by examiner

Primary Examiner—Floyd D. Higel
Assistant Examiner—Kamal Saeed
(74) Attorney, Agent, or Firm—Jacobson Holman, PLLC

(57) ABSTRACT

The invention relates to compounds of formula (I) wherein R1, R2, R3, R4 and Y have the meanings given in the description. Said compounds are novel active bronchial therapeutic agents.

9 Claims, No Drawings

BENZIMIDAZOLES AND BENZOXAZOLES

FIELD OF APPLICATION OF THE INVENTION

The invention relates to novel benzimidazoles and -oxazoles which are used in the pharmaceutical industry for the production of medicaments.

KNOWN TECHNICAL BACKGROUND

The international application WO94/12461 describes, inter alia, 2-(substituted phenyl)-benzimidazoles as selective inhibitors of phosphodiesterase type 4. The international application WO96/11917 discloses 2-(substituted phenyl)-benzoxazoles as selective PDE4 inhibitors.

DESCRIPTION OF THE INVENTION

It has now been found that the novel compounds of the general formula I described in greater detail below have surprising and particularly advantageous properties. Thus, the invention provides compounds of the formula I

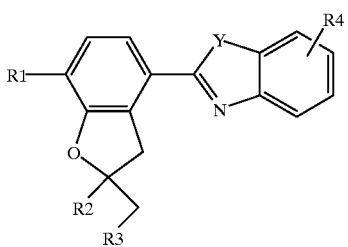

(I)

in which
Y is O (oxygen) or NH,
R1 is 1–4C-alkoxy, 3–7C-cycloalkoxy, 3–7C-cycloalkylmethoxy, benzyloxy or completely or predominantly fluorine-substituted 1–4C-alkoxy,
R2 is hydrogen or 1–4C-alkyl and
R3 is hydrogen or 1–4C-alkyl,
or in which
R2 and R3, together and including the two carbon atoms to which they are attached, are a spiro-linked 5-, 6- or 7-membered hydrocarbon ring which, if desired, is interrupted by an oxygen atom,
R4 is C(O)R5, C(O)R6, —$C_nH_{2n}$—C(O)R5 or —$C_nH_{2n}$—C(O)R6, where
R5 is hydroxyl, 1–7C-alkoxy, 3–7C-cycloalkoxy, 3–7C-cycloalkylmethoxy, $H_2N$—$C_mH_{2m}$—O— or R51 (R52)N—$C_pH_{2p}$—O—, where
R51 is hydrogen, 1–7C-alkyl, 3–7C-cycloalkyl or 3–7C-cycloalkylmethyl and
R52 is 1–7C-alkyl, 3–7C-cycloalkyl or 3–7C-cycloalkylmethyl, or where
R51 and R52, together and including the nitrogen atom to which both are attached, are a 5-, 6- or 7-membered hydrocarbon ring which, if desired, is additionally interrupted by a group —N(R7)— or an oxygen atom,
R6 is N(R61)R62, where R61 and R62 independently of one another are hydrogen, 1–7C-alkyl, 3–7C-cycloalkyl or 3–7C-cycloalkylmethyl,
R7 is hydrogen or 1–4C-alkyl,
m is 2, 3 or 4,
n is 1, 2, 3 or 4,
p is 1, 2, 3 or 4,
and the salts of these compounds.

1–4C-Alkyl represents a straight-chain or branched alkyl radical having 1 to 4 carbon atoms. Examples which may be mentioned are the butyl, isobutyl, sec-butyl, tert-butyl, propyl, isopropyl, ethyl and methyl radical.

1–7C-Alkyl represents straight-chain or branched alkyl radicals having 1 to 7 carbon atoms. Examples which may be mentioned are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radical.

1–4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radical.

3–7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As completely or predominantly fluorine-substituted 1–4C-alkoxy, for example, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radical may be mentioned.

Examples of spiro-linked 5-, 6- or 7-membered hydrocarbon rings which, if desired, are interrupted by an oxygen atom are, for example, the cyclopentane, cyclohexane, cyclopentane, tetrahydrofuran and tetrahydropyran ring.

Suitable radicals —$C_nH_{2n}$— and —$C_pH_{2p}$— are straight-chain or branched radicals having 1 to 4 carbon atoms. Examples which may be mentioned are the butylene, isobutylene, propylene, isopropylene, ethylene, 1-methylmethylene and methylene radical.

Suitable radicals —$C_mH_{2m}$— are straight-chain or branched radicals having 2 to 4 carbon atoms. Examples which may be mentioned are the butylene, isobutylene, propylene, isopropylene, ethylene and 1-methylmethylene radical.

1–7C-Alkoxy represents radicals which, in addition to the oxygen atom, contain a straight-chain or branched alkyl radical having 1 to 7 carbon atoms. Examples which may be mentioned are the heptyloxy, isoheptyloxy (5-methylhexyloxy), hexyloxy, isohexyloxy (4-methylpentyloxy), neohexyloxy (3,3-dimethylbutoxy), pentyloxy, isopentyloxy (3-methylbutoxy), neopentyloxy (2,2-dimethylpropoxy), butoxy, isobutoxy, sec-butoxy, tert-butoxy, propoxy and preferably the isopropoxy, ethoxy and methoxy radical.

Examples for the grouping R51(R52)N— in which R51 and R52, together and including the nitrogen atom to which both are attached, are a 5-, 6- or 7-membered hydrocarbon ring which, if desired, is additionally interrupted by a group —N(R7)— or an oxygen atom which may mentioned are the 4-methyl-1-piperazinyl, 1-piperazinyl, 1-pyrrolidinyl, 1-piperidyl, 1-hexahydroazepinyl and the 4-morpholinyl radical.

3–7C-Cycloalkyl represents cyclopropyl, cyclobutyl, cyclopentyl, cyclohexyl and cycloheptyl, of which cyclopropyl, cyclobutyl and cyclopentyl are preferred.

3–7C-Cycloalkylmethyl represents a methyl radical which is substituted by one of the abovementioned 3–7C- cycloalkyl radicals. The 3–5C-cycloalkylmethyl radicals cyclopropylmethyl, cyclobutylmethyl and cyclopentylmethyl may be mentioned as being preferred.

Possible salts for compounds of the formula I—depending on substitution—are all acid addition salts or all salts with bases. Particular mention may be made of the pharmacologically acceptable salts of the inorganic and organic acids customarily used in pharmacy. Those suitable are, on the one hand, water-soluble and water-insoluble acid addition salts with acids such a s, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, it being possible to employ the acids in salt preparation—depending on whether a mono- or polybasic acid is concerned and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminium, magnesium, titanium, ammonium, meglumine or guanidinium salts, where here too the bases are employed in salt preparation in an equimolar quantitative ratio or one differing therefrom.

Pharmacologically unacceptable salts which can initially be obtained, for example, as process products in the preparation of the compounds according to the invention on an industrial scale are converted into pharmacologically acceptable salts by processes known to the person skilled in the art.

It is known to the person skilled in the art that the compounds according to the invention and their salts, when they are isolated, for example, in crystalline form, can contain various amounts of solvents. The invention therefore also comprises all solvates and in particular all hydrates of the compounds of the formula 1, and also all solvates and in particular all hydrates of the salts of the compounds of the formula 1.

Compounds of the formula I to be emphasized are those in which

Y is O (oxygen) or NH,
R1 is 1–4C-alkoxy, 3–5C-cycloalkoxy, 3–5C-cycloalkylmethoxy, or completely or predominantly fluorine-substituted 1–2C-alkoxy,
R2 is 1–4C-alkyl and
R3 is hydrogen or 1–4C-alkyl, or in which
R2 and R3, together and including the two carbon atoms to which they are attached, are a spiro-linked cyclopentane, cyclohexane, tetrahydrofuran or tetrahydropyran ring,
R4 is C(O)R5, C(O)R6, —$C_nH_{2n}$—C(O)R5 or —$C_nH_{2n}$—C(O)R6, where
R5 is hydroxyl, 1–7C-alkoxy, 3–7C-cycloalkoxy, 3–7C-cycloalkylmethoxy, $H_2N$—$C_mH_{2m}$—O— or R51 (R52)N—$C_pH_{2p}$—O—, where
R51 is hydrogen or 1–4C-alkyl and
R52 is 1–4C-alkyl, or where
R51 and R52, together and including the nitrogen atom to which both are attached, are a 5-, 6- or 7-membered hydrocarbon ring which, if desired, is additionally interrupted by a group —N(R7)— or an oxygen atom,
R6 is N(R61)R62, where R61 and R62 independently of one another are hydrogen or 1–4C-alkyl,
R7 is hydrogen or 1–4C-alkyl,
m is 2,3or 4,
n is 1 or 2,
p is 1,2,3or 4,
and the salts of these compounds.

Compounds of the formula I to be emphasized in particular are those in which

Y is O (oxygen) or NH,
R1 is methoxy, ethoxy, cyclopropylmethoxy or completely or predominantly fluorine-substituted 1–2C-alkoxy,
R2 and R3, together and including the two carbon atoms to which they are attached, are a spiro-linked cyclopentane, cyclohexane, tetrahydrofuran or tetrahydropyran ring,
R4 is C(O)R5, C(O)R6, —$C_nH_{2n}$—C(O)R5 or —$C_nH_{2n}$—C(O)R6, where
R5 is hydroxyl, 1–4C-alkoxy or R51 (R52)N—$C_pH_{2p}$—O—, where
R51 is hydrogen or 1–4C-alkyl and
R52 is 1–4C-alkyl, or where
R51 and R52, together and including the nitrogen atom to which both are attached, are a 6-membered hydrocarbon ring which, if desired, is interrupted by a group —N(R7)— or an oxygen atom,
R6 is N(R61)R62, where R61 and R62 independently of one another are hydrogen or 1–4C-alkyl,
R7 is hydrogen or 1–4C-alkyl,
n is 1 or 2,
p is 1,2, 3or 4,
and the salts of these compounds.

Preferred compounds of the formula I are those in which

Y is O (oxygen) or NH,
R1 is methoxy,
R2 and R3, together and including the two carbon atoms to which they are attached, are a spiro-linked cyclopentane or tetrahydropyran ring,
R4 is carboxyl, carboxymethyl, carboxymethylmethyl, methoxycarbonylmethyl, methoxycarbonylmethylmethyl, methoxycarbonyl, aminocarbonyl or morpholin-4-ylethyleneoxycarbonyl,
and the salts of these compounds.

Particularly preferred compounds of the formula I are those in which

Y is O (oxygen) or NH,
R1 is methoxy,
R2 and R3, together and including the two carbon atoms to which they are attached, are a spiro-linked cyclopentane ring,
R4 is carboxyl, carboxymethyl, carboxymethylmethyl, methoxycarbonylmethyl, methoxycarbonylmethylmethyl, methoxycarbonyl, aminocarbonyl or morpholin-4-ylethyleneoxycarbonyl,
and the salts of these compounds.

Examples of compounds according to the invention are listed in the tables below:

TABLE 1

Compounds of the formula I where Y = NH, R4 = C(O)OH
(in the 5-position of the benzimidazole ring system)
and the following further substituent meanings:

| R1 | R2 | R3 |
|---|---|---|
| $OCH_3$ | $CH_3$ | H |
| $OC_2H_5$ | $CH_3$ | H |
| $OCF_2H$ | $CH_3$ | H |
| $OCF_3$ | $CH_3$ | H |
| $OCH_3$ | $C_2H_5$ | $CH_3$ |
| $OC_2H_5$ | $C_2H_5$ | $CH_3$ |

TABLE 1-continued

Compounds of the formula I where Y = NH, R4 = C(O)OH
(in the 5-position of the benzimidazole ring system)
and the following further substituent meanings:

| R1 | R2 | R3 |
|---|---|---|
| $OCF_2H$ | $C_2H_5$ | $CH_3$ |
| $OCF_3$ | $C_2H_5$ | $CH_3$ |
| $OCH_3$ | $CH_2CH_2CH_2$ | |
| $OC_2H_5$ | $CH_2CH_2CH_2$ | |
| $OCF_2H$ | $CH_2CH_2CH_2$ | |
| $OCF_3$ | $CH_2CH_2CH_2$ | |
| $OCH_3$ | $CH_2CH_2CH_2CH_2$ | |
| $OC_2H_5$ | $CH_2CH_2CH_2CH_2$ | |
| $OCF_2H$ | $CH_2CH_2CH_2CH_2$ | |
| $OCF_3$ | $CH_2CH_2CH_2CH_2$ | |
| $OCH_3$ | $CH_2-O-CH_2$ | |
| $OC_2H_5$ | $CH_2-O-CH_2$ | |
| $OCF_2H$ | $CH_2-O-CH_2$ | |
| $OCF_3$ | $CH_2-O-CH_2$ | |
| $OCH_3$ | $CH_2CH_2-O$ | |
| $OC_2H_5$ | $CH_2CH_2-O$ | |
| $OCF_2H$ | $CH_2CH_2-O$ | |
| $OCF_3$ | $CH_2CH_2-O$ | |
| $OCH_3$ | $CH_2CH_2-O-CH_2$ | |
| $OC_2H_5$ | $CH_2CH_2-O-CH_2$ | |
| $OCF_2H$ | $CH_2CH_2-O-CH_2$ | |
| $OCF_3$ | $CH_2CH_2-O-CH_2$ | |

TABLE 2

Compounds of the formula I where Y = O, R4 = C(O)OH
(in the 5-position of the benzoxazole ring system)
and the following further substituent meanings:

| R1 | R2 | R3 |
|---|---|---|
| $OCH_3$ | $CH_3$ | H |
| $OC_2H_5$ | $CH_3$ | H |
| $OCF_2H$ | $CH_3$ | H |
| $OCF_3$ | $CH_3$ | H |
| $OCH_3$ | $C_2H_5$ | $CH_3$ |
| $OC_2H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_3$ | $CH_2CH_2CH_2$ | |
| $OC_2H_5$ | $CH_2CH_2CH_2$ | |
| $OCF_2H$ | $CH_2CH_2CH_2$ | |
| $OCF_3$ | $CH_2CH_2CH_2$ | |
| $OCH_3$ | $CH_2CH_2CH_2CH_2$ | |
| $OC_2H_5$ | $CH_2CH_2CH_2CH_2$ | |
| $OCF_2H$ | $CH_2CH_2CH_2CH_2$ | |
| $OCF_3$ | $CH_2CH_2CH_2CH_2$ | |
| $OCH_3$ | $CH_2-O-CH_2$ | |
| $OC_2H_5$ | $CH_2-O-CH_2$ | |
| $OCF_2H$ | $CH_2-O-CH_2$ | |
| $OCF_3$ | $CH_2-O-CH_2$ | |
| $OCH_3$ | $CH_2CH_2-O$ | |
| $OC_2H_5$ | $CH_2CH_2-O$ | |
| $OCF_2H$ | $CH_2CH_2-O$ | |
| $OCF_3$ | $CH_2CH_2-O$ | |
| $OCH_3$ | $CH_2CH_2-O-CH_2$ | |
| $OC_2H_5$ | $CH_2CH_2-O-CH_2$ | |
| $OCF_2H$ | $CH_2CH_2-O-CH_2$ | |
| $OCF_3$ | $CH_2CH_2-O-CH_2$ | |

TABLE 3

Compounds of the formula I where Y = O, R4 = C(O)OH
(in the 6-position of the benzoxazole ring system)
and the following further substituent meanings:

| R1 | R2 | R3 |
|---|---|---|
| $OCH_3$ | $CH_3$ | H |
| $OC_2H_5$ | $CH_3$ | H |
| $OCF_2H$ | $CH_3$ | H |
| $OCF_3$ | $CH_3$ | H |
| $OCH_3$ | $C_2H_5$ | $CH_3$ |
| $OC_2H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_3$ | $CH_2CH_2CH_2$ | |
| $OC_2H_5$ | $CH_2CH_2CH_2$ | |
| $OCF_2H$ | $CH_2CH_2CH_2$ | |
| $OCF_3$ | $CH_2CH_2CH_2$ | |
| $OCH_3$ | $CH_2CH_2CH_2CH_2$ | |
| $OC_2H_5$ | $CH_2CH_2CH_2CH_2$ | |
| $OCF_2H$ | $CH_2CH_2CH_2CH_2$ | |
| $OCF_3$ | $CH_2CH_2CH_2CH_2$ | |
| $OCH_3$ | $CH_2-O-CH_2$ | |
| $OC_2H_5$ | $CH_2-O-CH_2$ | |
| $OCF_2H$ | $CH_2-O-CH_2$ | |
| $OCF_3$ | $CH_2-O-CH_2$ | |
| $OCH_3$ | $CH_2CH_2-O$ | |
| $OC_2H_5$ | $CH_2CH_2-O$ | |
| $OCF_2H$ | $CH_2CH_2-O$ | |
| $OCF_3$ | $CH_2CH_2-O$ | |
| $OCH_3$ | $CH_2CH_2-O-CH_2$ | |
| $OC_2H_5$ | $CH_2CH_2-O-CH_2$ | |
| $OCF_2H$ | $CH_2CH_2-O-CH_2$ | |
| $OCF_3$ | $CH_2CH_2-O-CH_2$ | |

TABLE 4

Compounds of the formula I where Y = NH, R4 = C(O)OCH$_3$
(in the 5-position of the benzimidazole ring system)
and the following further substituent meanings:

| R1 | R2 | R3 |
|---|---|---|
| $OCH_3$ | $CH_3$ | H |
| $OC_2H_5$ | $CH_3$ | H |
| $OCF_2H$ | $CH_3$ | H |
| $OCF_3$ | $CH_3$ | H |
| $OCH_3$ | $C_2H_5$ | $CH_3$ |
| $OC_2H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_3$ | $CH_2CH_2CH_2$ | |
| $OC_2H_5$ | $CH_2CH_2CH_2$ | |
| $OCF_2H$ | $CH_2CH_2CH_2$ | |
| $OCF_3$ | $CH_2CH_2CH_2$ | |
| $OCH_3$ | $CH_2CH_2CH_2CH_2$ | |
| $OC_2H_5$ | $CH_2CH_2CH_2CH_2$ | |
| $OCF_2H$ | $CH_2CH_2CH_2CH_2$ | |
| $OCF_3$ | $CH_2CH_2CH_2CH_2$ | |
| $OCH_3$ | $CH_2-O-CH_2$ | |
| $OC_2H_5$ | $CH_2-O-CH_2$ | |
| $OCF_2H$ | $CH_2-O-CH_2$ | |
| $OCF_3$ | $CH_2-O-CH_2$ | |
| $OCH_3$ | $CH_2CH_2-O$ | |
| $OC_2H_5$ | $CH_2CH_2-O$ | |
| $OCF_2H$ | $CH_2CH_2-O$ | |
| $OCF_3$ | $CH_2CH_2-O$ | |
| $OCH_3$ | $CH_2CH_2-O-CH_2$ | |
| $OC_2H_5$ | $CH_2CH_2-O-CH_2$ | |
| $OCF_2H$ | $CH_2CH_2-O-CH_2$ | |
| $OCF_3$ | $CH_2CH_2-O-CH_2$ | |

TABLE 5

Compounds of the formula I where Y = O, R4 = C(O)OCH$_3$
(in the 5-position of the benzoxazole ring system)
and the following further substituent meanings:

| R1 | R2 | | R3 |
|---|---|---|---|
| OCH$_3$ | CH$_3$ | | H |
| OC$_2$H$_5$ | CH$_3$ | | H |
| OCF$_2$H | CH$_3$ | | H |
| OCF$_3$ | CH$_3$ | | H |
| OCH$_3$ | C$_2$H$_5$ | | CH$_3$ |
| OC$_2$H$_5$ | C$_2$H$_5$ | | CH$_3$ |
| OCF$_2$H | C$_2$H$_5$ | | CH$_3$ |
| OCF$_3$ | C$_2$H$_5$ | | CH$_3$ |
| OCH$_3$ | | CH$_2$CH$_2$CH$_2$ | |
| OC$_2$H$_5$ | | CH$_2$CH$_2$CH$_2$ | |
| OCF$_2$H | | CH$_2$CH$_2$CH$_2$ | |
| OCF$_3$ | | CH$_2$CH$_2$CH$_2$ | |
| OCH$_3$ | | CH$_2$CH$_2$CH$_2$CH$_2$ | |
| OC$_2$H$_5$ | | CH$_2$CH$_2$CH$_2$CH$_2$ | |
| OCF$_2$H | | CH$_2$CH$_2$CH$_2$CH$_2$ | |
| OCF$_3$ | | CH$_2$CH$_2$CH$_2$CH$_2$ | |
| OCH$_3$ | | CH$_2$—O—CH$_2$ | |
| OC$_2$H$_5$ | | CH$_2$—O—CH$_2$ | |
| OCF$_2$H | | CH$_2$—O—CH$_2$ | |
| OCF$_3$ | | CH$_2$—O—CH$_2$ | |
| OCH$_3$ | | CH$_2$CH$_2$—O | |
| OC$_2$H$_5$ | | CH$_2$CH$_2$—O | |
| OCF$_2$H | | CH$_2$CH$_2$—O | |
| OCF$_3$ | | CH$_2$CH$_2$—O | |
| OCH$_3$ | | CH$_2$CH$_2$—O—CH$_2$ | |
| OC$_2$H$_5$ | | CH$_2$CH$_2$—O—CH$_2$ | |
| OCF$_2$H | | CH$_2$CH$_2$—O—CH$_2$ | |
| OCF$_3$ | | CH$_2$CH$_2$—O—CH$_2$ | |

TABLE 6

Compounds of the formula I where Y = O, R4 = C(O)OCH$_3$
(in the 6-position of the benzoxazole ring system)
and the following further substituent meanings:

| R1 | R2 | | R3 |
|---|---|---|---|
| OCH$_3$ | CH$_3$ | | H |
| OC$_2$H$_5$ | CH$_3$ | | H |
| OCF$_2$H | CH$_3$ | | H |
| OCF$_3$ | CH$_3$ | | H |
| OCH$_3$ | C$_2$H$_5$ | | CH$_3$ |
| OC$_2$H$_5$ | C$_2$H$_5$ | | CH$_3$ |
| OCF$_2$H | C$_2$H$_5$ | | CH$_3$ |
| OCF$_3$ | C$_2$H$_5$ | | CH$_3$ |
| OCH$_3$ | | CH$_2$CH$_2$CH$_2$ | |
| OC$_2$H$_5$ | | CH$_2$CH$_2$CH$_2$ | |
| OCF$_2$H | | CH$_2$CH$_2$CH$_2$ | |
| OCF$_3$ | | CH$_2$CH$_2$CH$_2$ | |
| OCH$_3$ | | CH$_2$CH$_2$CH$_2$CH$_2$ | |
| OC$_2$H$_5$ | | CH$_2$CH$_2$CH$_2$CH$_2$ | |
| OCF$_2$H | | CH$_2$CH$_2$CH$_2$CH$_2$ | |
| OCF$_3$ | | CH$_2$CH$_2$CH$_2$CH$_2$ | |
| OCH$_3$ | | CH$_2$—O—CH$_2$ | |
| OC$_2$H$_5$ | | CH$_2$—O—CH$_2$ | |
| OCF$_2$H | | CH$_2$—O—CH$_2$ | |
| OCF$_3$ | | CH$_2$—O—CH$_2$ | |
| OCH$_3$ | | CH$_2$CH$_2$—O | |
| OC$_2$H$_5$ | | CH$_2$CH$_2$—O | |
| OCF$_2$H | | CH$_2$CH$_2$—O | |
| OCF$_3$ | | CH$_2$CH$_2$—O | |
| OCH$_3$ | | CH$_2$CH$_2$—O—CH$_2$ | |
| OC$_2$H$_5$ | | CH$_2$CH$_2$—O—CH$_2$ | |
| OCF$_2$H | | CH$_2$CH$_2$—O—CH$_2$ | |
| OCF$_3$ | | CH$_2$CH$_2$—O—CH$_2$ | |

TABLE 7

Compounds of the formula I where Y = NH, R4 = C(O)NH$_2$
(in the 5-position of the benzimidazole ring system)
and the following further substituent meanings:

| R1 | R2 | | R3 |
|---|---|---|---|
| OCH$_3$ | CH$_3$ | | H |
| OC$_2$H$_5$ | CH$_3$ | | H |
| OCF$_2$H | CH$_3$ | | H |
| OCF$_3$ | CH$_3$ | | H |
| OCH$_3$ | C$_2$H$_5$ | | CH$_3$ |
| OC$_2$H$_5$ | C$_2$H$_5$ | | CH$_3$ |
| OCF$_2$H | C$_2$H$_5$ | | CH$_3$ |
| OCF$_3$ | C$_2$H$_5$ | | CH$_3$ |
| OCH$_3$ | | CH$_2$CH$_2$CH$_2$ | |
| OC$_2$H$_5$ | | CH$_2$CH$_2$CH$_2$ | |
| OCF$_2$H | | CH$_2$CH$_2$CH$_2$ | |
| OCF$_3$ | | CH$_2$CH$_2$CH$_2$ | |
| OCH$_3$ | | CH$_2$CH$_2$CH$_2$CH$_2$ | |
| OC$_2$H$_5$ | | CH$_2$CH$_2$CH$_2$CH$_2$ | |
| OCF$_2$H | | CH$_2$CH$_2$CH$_2$CH$_2$ | |
| OCF$_3$ | | CH$_2$CH$_2$CH$_2$CH$_2$ | |
| OCH$_3$ | | CH$_2$—O—CH$_2$ | |
| OC$_2$H$_5$ | | CH$_2$—O—CH$_2$ | |
| OCF$_2$H | | CH$_2$—O—CH$_2$ | |
| OCF$_3$ | | CH$_2$—O—CH$_2$ | |
| OCH$_3$ | | CH$_2$CH$_2$—O | |
| OC$_2$H$_5$ | | CH$_2$CH$_2$—O | |
| OCF$_2$H | | CH$_2$CH$_2$—O | |
| OCF$_3$ | | CH$_2$CH$_2$—O | |
| OCH$_3$ | | CH$_2$CH$_2$—O—CH$_2$ | |
| OC$_2$H$_5$ | | CH$_2$CH$_2$—O—CH$_2$ | |
| OCF$_2$H | | CH$_2$CH$_2$—O—CH$_2$ | |
| OCF$_3$ | | CH$_2$CH$_2$—O—CH$_2$ | |

TABLE 8

Compounds of the formula I where Y = O, R4 = C(O)NH$_2$
(in the 5-position of the benzoxazole ring system)
and the following further substituent meanings:

| R1 | R2 | | R3 |
|---|---|---|---|
| OCH$_3$ | CH$_3$ | | H |
| OC$_2$H$_5$ | CH$_3$ | | H |
| OCF$_2$H | CH$_3$ | | H |
| OCF$_3$ | CH$_3$ | | H |
| OCH$_3$ | C$_2$H$_5$ | | CH$_3$ |
| OC$_2$H$_5$ | C$_2$H$_5$ | | CH$_3$ |
| OCF$_2$H | C$_2$H$_5$ | | CH$_3$ |
| OCF$_3$ | C$_2$H$_5$ | | CH$_3$ |
| OCH$_3$ | | CH$_2$CH$_2$CH$_2$ | |
| OC$_2$H$_5$ | | CH$_2$CH$_2$CH$_2$ | |
| OCF$_2$H | | CH$_2$CH$_2$CH$_2$ | |
| OCF$_3$ | | CH$_2$CH$_2$CH$_2$ | |
| OCH$_3$ | | CH$_2$CH$_2$CH$_2$CH$_2$ | |
| OC$_2$H$_5$ | | CH$_2$CH$_2$CH$_2$CH$_2$ | |
| OCF$_2$H | | CH$_2$CH$_2$CH$_2$CH$_2$ | |
| OCF$_3$ | | CH$_2$CH$_2$CH$_2$CH$_2$ | |
| OCH$_3$ | | CH$_2$—O—CH$_2$ | |
| OC$_2$H$_5$ | | CH$_2$—O—CH$_2$ | |
| OCF$_2$H | | CH$_2$—O—CH$_2$ | |
| OCF$_3$ | | CH$_2$—O—CH$_2$ | |
| OCH$_3$ | | CH$_2$CH$_2$—O | |
| OC$_2$H$_5$ | | CH$_2$CH$_2$—O | |
| OCF$_2$H | | CH$_2$CH$_2$—O | |
| OCF$_3$ | | CH$_2$CH$_2$—O | |
| OCH$_3$ | | CH$_2$CH$_2$—O—CH$_2$ | |
| OC$_2$H$_5$ | | CH$_2$CH$_2$—O—CH$_2$ | |
| OCF$_2$H | | CH$_2$CH$_2$—O—CH$_2$ | |
| OCF$_3$ | | CH$_2$CH$_2$—O—CH$_2$ | |

TABLE 9

Compounds of the formula I where Y = O, R4 = C(O)NH$_2$
(in the 6-position of the benzoxazole ring system)
and the following further substituent meanings:

| R1 | R2 | R3 |
|---|---|---|
| OCH$_3$ | CH$_3$ | H |
| OC$_2$H$_5$ | CH$_3$ | H |
| OCF$_2$H | CH$_3$ | H |
| OCF$_3$ | CH$_3$ | H |
| OCH$_3$ | C$_2$H$_5$ | CH$_3$ |
| OC$_2$H$_5$ | C$_2$H$_5$ | CH$_3$ |
| OCF$_2$H | C$_2$H$_5$ | CH$_3$ |
| OCF$_3$ | C$_2$H$_5$ | CH$_3$ |
| OCH$_3$ | | CH$_2$CH$_2$CH$_2$ |
| OC$_2$H$_5$ | | CH$_2$CH$_2$CH$_2$ |
| OCF$_2$H | | CH$_2$CH$_2$CH$_2$ |
| OCF$_3$ | | CH$_2$CH$_2$CH$_2$ |
| OCH$_3$ | | CH$_2$CH$_2$CH$_2$CH$_2$ |
| OC$_2$H$_5$ | | CH$_2$CH$_2$CH$_2$CH$_2$ |
| OCF$_2$H | | CH$_2$CH$_2$CH$_2$CH$_2$ |
| OCF$_3$ | | CH$_2$CH$_2$CH$_2$CH$_2$ |
| OCH$_3$ | | CH$_2$—O—CH$_2$ |
| OC$_2$H$_5$ | | CH$_2$—O—CH$_2$ |
| OCF$_2$H | | CH$_2$—O—CH$_2$ |
| OCF$_3$ | | CH$_2$—O—CH$_2$ |
| OCH$_3$ | | CH$_2$CH$_2$—O |
| OC$_2$H$_5$ | | CH$_2$CH$_2$—O |
| OCF$_2$H | | CH$_2$CH$_2$—O |
| OCF$_3$ | | CH$_2$CH$_2$—O |
| OCH$_3$ | | CH$_2$CH$_2$—O—CH$_2$ |
| OC$_2$H$_5$ | | CH$_2$CH$_2$—O—CH$_2$ |
| OCF$_2$H | | CH$_2$CH$_2$—O—CH$_2$ |
| OCF$_3$ | | CH$_2$CH$_2$—O—CH$_2$ | and the salts of the compounds mentioned in the tables.

If Y is NH, the compounds of the formula I can be tautomers and —if the substituents —R2 and —CH$_2$R3 are not identical—chiral compounds. The invention therefore comprises both the pure tautomers and enantiomers and mixtures thereof in any mixing ratio, including the racemates. The enantiomers can be separated in a manner known per se (for example by preparing and separating corresponding diastereoisomeric compounds).

However, preference is given to the compounds of the formula I in which the substituents —R2 and —CH$_2$R3 are identical or in which R2 and R3, together and including the two carbon atoms to which they are attached, are a spiro-linked 5-, 6- or 7-membered hydrocarbon ring. Preference is furthermore given to the compounds of the formula I in which R2 and R3, together and including the two carbon atoms to which they are attached, are a spiro-linked 4'-tetrahydropyran ring.

At the benzimidazole or -oxazole ring system, the substituent R4 can be attached in the 4-, 5-, 6- or 7-position; however, preference is given to the compounds of the formula I in which the substituent is attached in the 5- or 6-position.

The invention also provides a process for preparing the compounds of the formula I and their salts. The process (cf. scheme 1) is characterized in that compounds of the formula 11 in which R1, R2 and R3 are as defined above and Z is a suitable leaving group are reacted with compounds of the formula III in which Y is O (oxygen) or NH and R4 has the meanings given above.

Scheme 1

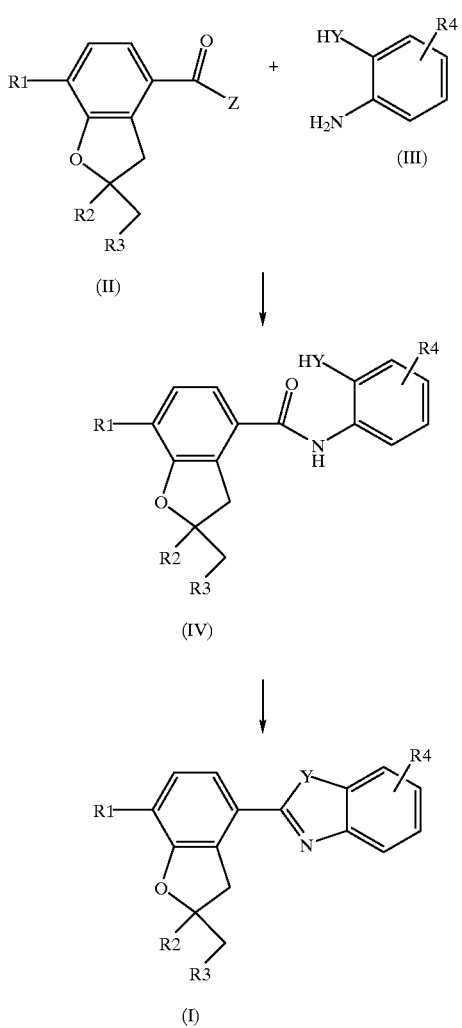

Suitable leaving groups Z are known to the person skilled in the art owing to his expert knowledge. Suitable acyl halides of the formula 11 (Z=Cl or Br), for example, can be used as starting materials.

The reaction of the compounds of the formula II with compounds of the formula III is preferably carried out in the presence of a base, such as, for example, pyridine or triethylamine, in a suitable inert solvent, for example in a cyclic hydrocarbon, such as toluene or xylene, or in any other inert solvent, such as dioxane, or without additional solvent, preferably at elevated temperature.

The compounds of the formula IV, in which R1, R2, R3, R4 and Y are as defined above, which are initially formed in the reaction are converted by intramolecular condensation into the corresponding compounds of the formula I. This intramolecular condensation can be carried out, for example, thermally by simple heating; however, it is preferably carried out in the presence of a suitable condensing agent, such as, for example, thionyl chloride or phosphorus oxytrichloride, in a suitable inert solvent or without additional solvent using an excess of condensing agent, preferably at elevated temperature, in particular at the boiling point of the solvent or condensing agent used.

The reaction is, for example, carried out as described in the examples below, or in a manner known per se to the person skilled in the art, for example as described in the international application WO94/12461.

The resulting compounds of the formula I can then be converted into their salts, and any salts of the compounds of the formula I which are obtained can be converted into the free compounds.

Compounds of the formula II in which Z is a suitable leaving group and R1, R2 and R3 have the meanings given above can be prepared as described in the examples below or in a manner which is familiar to the person skilled in the art, from the corresponding compounds of the formula II in which Z is a hydroxyl group and R1, R2 and R3 have the meanings given above.

Compounds of the formula II in which Z is a hydroxyl group and R1, R2 and R3 have the meanings given above can be obtained as described in WO96/03399, or by methods and techniques which are familiar to the person skilled in the art.

Compounds of the formula III are known or can be prepared in a manner known per se to the person skilled in the art, using customary processes.

It is moreover known to the person skilled in the art that if there are a number of reactive centres on a starting material or intermediate it may be necessary to block one or more reactive centres temporarily by protective groups in order to allow a reaction to proceed specifically at the desired reaction centre. A detailed description for the use of a large number of proven protective groups is found, for example, in T. W. Greene, Protective Groups in Organic Synthesis, John Wiley & Sons, 1991.

If desired, compounds of the formula I obtained can be converted into other compounds of the formula I by derivatization. In this manner, it is possible to obtain, for example, the corresponding acids (R4=—$C_nH_{2n}$—COOH, COOH) from compounds of the formula I in which R1, R2 and R3 are as defined above and R4 comprises an ester group, by acidic or alkaline hydrolysis, or to prepare the corresponding amides by reaction with amines of the formula HN(R61)R62, in which R61 and R62 have the meanings given above. The reactions are advantageously carried out analogously to methods known to the person skilled in the art, for example as described in the examples below.

The isolation and purification of the substances according to the invention is carried out in a manner known per se, for example by distilling off the solvent in vacuo and recrystallizing the resulting residue from a suitable solvent or subjecting it to one of the customary purification methods, such as, for example, column chromatography on a suitable support material.

Salts are obtained by dissolving the free compound in a suitable solvent (for example a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically unacceptable salts can be converted into pharmacologically acceptable salts.

The following examples serve to illustrate the invention further without restricting it. Likewise, further compounds of the formula I, whose preparation is not explicitly described, can be prepared in an analogous manner or in a manner familiar per se to the person skilled in the art using customary process techniques.

In the examples, m.p. denotes melting point, h denotes hour(s), min denotes minute(s), RT denotes room temperature, EF denotes empirical formula and MW denotes molecular weight. The compounds mentioned in the examples and their salts are a preferred subject of the invention.

EXAMPLES

End Products 1. 2-(2,3-Dihydro-7-methoxybenzofuran-2-spiro-1'-cyclopentan-4-yl)benzimidazole-5-carboxylic acid 3.44 g (9.1 mmol) of methyl 2-(2,3-dihydro-7-methoxybenzofuran-2-spiro-1'-cyclopentan-4-yl)benzimidazole-5-carboxylate (compound 13) in 50 ml of 4 N sodium hydroxide solution are heated at reflux for 3 h. The mixture is allowed to cool and diluted with 100 ml of water, and 100 ml of 2 N hydrochloric acid are slowly added dropwise with stirring. The product is filtered off and dried under high vacuum. This gives 3.06 g of the title compound of m.p. 235–240° C.

2. 2-(2,3-Dihydro-7-methoxybenzofuran-2-spiro-1'-cyclopentan-4-yl)benzimidazole-5-carboxamide 500 mg (1.37 mmol) of 2-(2,3-dihydro-7-methoxybenzofuran-2-spiro-1'-cyclopentan-4-yl)benzimidazole-5-carboxylic acid (compound 1) in 10 ml of thionyl chloride are heated at reflux for 45 min. Excess thionyl chloride is removed in vacuo and the residue is co-evaporated repeatedly with toluene. The residue is suspended in 5 ml of acetone and 5 ml of concentrated ammonia are added dropwise with ice-cooling. The mixture is then allowed to warm to RT. After the reaction has ended (TLC control), the mixture is diluted with 50 ml of water and extracted with ethyl acetate. The organic phases are collected, dried over magnesium sulphate and concentrated. The residue is crystallized from methanol, giving 180 mg of the title compound of m.p. 245° C.

3. 2-(2,3-Dihydro-7-methoxybenzofuran-2-spiro-1'-cyclopentan-4-yl)benzoxazole-5-carboxylic acid A suspension of 120 mg (0.32 mmol) of methyl 2-(2,3-dihydro-7-methoxybenzofuran-2-spiro-1'-cyclo-pentan-4-yl)benzoxazole-5-carboxylate (compound 14) in a mixture of 10 ml of water and 10 ml of ethanol is admixed with 40 mg (0.83 mmol) of lithium hydroxide and stirred at 60° C. for 24 h. The mixture is neutralized with half-concentrated hydrochloric acid and extracted with 2×20 ml of ethyl acetate. The combined organic phases are dried over magnesium sulphate and concentrated until crystallization starts. The crystal slurry is filtered off with suction and dried, giving 70 mg of the title compound of m.p.>250° C.

4. 2-(2,3-Dihydro-7-methoxybenzofuran-2-spiro-1'-cyclopentan-4-yl)benzoxazol-5-ylacetic acid 100 mg (0.25 mmol) of methyl 2-(2,3-dihydro-7-methoxybenzofuran-2-spiro-1'-cyclopentan-4-yl)benzoxazol-5-ylacetate (compound 15) and 30 mg of lithium hydroxide (1.25 mmol) are stirred in a mixture of 5 ml of water and 5 ml of ethanol at RT overnight. The mixture is diluted with 10 ml of water, admixed with 1 ml of 2 N hydrochloric acid and extracted with 2×30 ml of ethyl acetate. The combined organic phases are then dried over magnesium sulphate and concentrated, and the residue is triturated with diethyl ether. This gives 80 mg of the title compound of m.p. 220° C.

5. 2-[2-(2,3-Dihydro-7-methoxybenzofuran-2-spiro-1'-cyclopentan-4-yl)benzoxazol-5-yl]propionic acid With ice-cooling, hydrogen chloride is introduced into a solution of 200 mg (0.53 mmol) of 2-[2-(2,3-dihydro-7- methoxybenzofuran-2-spiro-1'-cyclopentan-4-yl) benzoxazol-5-yl]propionitrile (starting material A1) in 50 ml of methanol until saturation is reached. The reaction solution is allowed to stand in a refrigerator for 5 days. The methanolic hydrochloric acid solution is then removed under reduced pressure and the residue is co-evaporated twice with toluene. The residue is taken up in 10 ml of glycerol, admixed with 500 mg of potassium hydroxide and heated at 160° C. for 1 h. The mixture is then acidified with 20 ml of 1 N hydrochloric acid and extracted with ethyl acetate, and the organic phase is washed with saturated sodium chloride solution, dried over magnesium sulphate and concentrated. The residue is dissolved in 10 ml of 0.1 N aqueous sodium hydroxide solution, the solution is clarified using kieselguhr and the product is precipitated using 15 ml of 0.1 N hydrochloric acid. This gives 145 mg of the title compound of m.p. 90–105° C. (decomp.).

6. 2-(2,3-Dihydro-7-methoxybenzofuran-2-spiro-4'-tetrahydropyran-4-yl)benzoxazole-5-carboxylic acid A suspension of 1.16 g (2.8 mmol) of methyl 2-(2,3-dihydro-7-methoxybenzofuran-2-spiro-4'-tetra-hydropyran-4-yl)benzoxazole-5-carboxylate (compound 16) in a mixture of 100 ml of water and 20 ml of ethanol is admixed with 540 mg (22.4 mmol) of lithium hydroxide and stirred at RT for 48 h. The ethanol is evaporated, a further 30 ml of water are added and the reaction mixture is, with stirring and ice-cooling, acidified to pH=1–2 by dropwise addition of 2 N hydrochloric acid. The precipitate is filtered off with suction and dried over potassium hydroxide. This gives 1.04 g of the title compound of m.p. 251–253° C.

7. 2-(2,3-Dihydro-7-methoxybenzofuran-2-spiro-4'-tetrahydropyran-4-yl)benzoxazole-5-carboxamide 300 mg (0.69 mmol) of 2-(2,3-dihydro-7-methoxybenzofuran-2-spiro-4'-tetrahydropyran-4-yl) benzoxazole-5-carboxylic acid (compound 6) in 1 ml of thionyl chloride are heated at reflux for 30 min. Excess thionyl chloride is removed under reduced pressure and the residue is co-evaporated repeatedly with toluene. The residue is suspended in 20 ml of acetone and 6 ml of concentrated ammonia are added dropwise with ice-cooling. The mixture is then allowed to warm to RT. After the reaction has ended (TLC control), the acetone is distilled off and the reaction mixture is diluted with 10 ml of water. The precipitate is filtered off, washed with cold water and cold acetone and dried over potassium hydroxide. This gives 260 mg of the title compound of m.p. 238–240° C.

8. 2-(2,3-Dihydro-7-methoxybenzofuran-2-spiro-1'-cyclopentan-4-yl)benzoxazole-6-carboxylic acid 1.8 g (4.75 mmol) of methyl 2-(2,3-dihydro-7-methoxybenzofuran-2-spiro-1'-cyclopentan-4-yl) benzoxazole-6-carboxylate (compound 17) in 30 ml of 4 N aqueous sodium hydroxide solution and 30 ml of methanol are heated at 80° C. for 1 hour. The reaction mixture is allowed to cool and diluted with 300 ml of water, and 20 ml of half-concentrated hydrochloric acid are slowly added dropwise with stirring. The product is filtered off and dried under high vacuum. This gives 0.95 g of the title compound of m.p. >250° C.

9. 2-morpholin-4-ylethyl 2-(2,3-dihydro-7-methoxybenzofuran-2-spiro-1'-cyclopentan4-yl)-benzoxazole-6-carboxylate 1.5 g (4.1 mmol) of 2-(2,3-dihydro-7-methoxybenzofuran-2-spiro-1'-cyclopentan-4-yl) benzoxazole-6-carboxylic acid (compound 8) in 10 ml of thionyl chloride are heated at reflux for 45 min. The mixture is allowed to cool and concentrated and co-evaporated repeatedly with toluene. Over a period of 15 min, the residue is added a little at a time to a solution of 1.49 ml (12.3 mmol) of N-(2-hydroxyethyl)morpholine and 33 pl (0.41 mmol) of pyridine in 30 ml of dioxane. After 20 min, the mixture is filtered and the filtrate is concentrated. The residue is chromatographed over silica gel [ethyl acetate]. The product crystallizes from acetonitrile. This gives 1.49 g of the title compound of m.p. 143–144° C.

10. 2-[2-(2,3-Dihydro-7-methoxybenzofuran-2-spiro-1'-cyclopentan-4-yl)benzoxazol-6-yl]-propionic acid 1.3 g (3 mmol) of ethyl 2-{4-[(2,3-dihydro-7-methoxybenzofuran-2-spiro-1'-cyclopentane-4-carbonyl) amino]-3-hydroxyphenyl}propionate (starting material A8) are heated at 240° C. for 4 h. The reaction mixture is chromatographed over silica gel [toluene/ethyl acetate=5:1]. The product, ethyl 2-[2-(2,3-dihydro-7-methoxybenzofuran-2-spiro-1'-cyclopentan-4-yl )benzoxazol-6-yl]propionate, is taken up in 20 ml of ethanol and 10 ml of water, and the solution is admixed with 240 mg (10 mmol) of lithium hydroxide. The mixture is stirred at RT for 16 h, most of the ethanol is distilled off and the mixture is extracted with ethyl acetate. The combined organic phases are dried over magnesium sulphate and concentrated, and the residue is recrystallized from 5 ml of ethanol. This gives 430 mg of the title compound of m.p. 172–174° C.

11. 2-(2,3-Dihydro-7-methoxybenzofuran-2-spiro-4'-tetrahydropyran-4-yl) benzoxazole-6-carboxylic acid A suspension of 1.36 g (3.29 mmol) of methyl 2-(2,3-dihydro-7-methoxybenzofuran-2-spiro-4'-tetra-hydropyran-4-yl)benzoxazole-6-carboxylate (compound 18) in a mixture of 100 ml of water and 20 ml of ethanol is admixed with 630 mg (26.2 mmol) of lithium hydroxide and stirred at RT for 48 h. The ethanol is evaporated, a further 30 ml of water are added and the reaction mixture is acidified to pH=1–2 by dropwise addition of 2 N hydrochloric acid, with stirring and ice-cooling. The precipitate is filtered off with suction and dried over potassium hydroxide. This gives 1.21 g of the title compound of m.p. >260° C.

12. 2-(2,3-Dihydro-7-methoxybenzofuran-2-spiro-4'-tetrahydropyran-4-yl)benzoxazole-6-carboxamide 300 mg (0.79 mmol) of 2-(2,3-dihydro-7-methoxybenzofuran-2-spiro-4'-tetrahydropyran4-yl)benzoxazole-6-carboxylic acid (compound 11) in 1 ml of thionyl chloride are heated at reflux for 30 min. Excess thionyl chloride is removed under reduced pressure and the residue is co-evaporated repeatedly with toluene. The residue is suspended in 20 ml of acetone and 6 ml of concentrated ammonia are added dropwise with ice-cooling. The precipitate is filtered off, washed with cold acetone and dried over potassium hydroxide. This gives 220 mg of the title compound of m.p. 262–264° C.

13. Methyl 2-(2,3-dihydro-7-methoxybenzofuran-2-spiro-1'-cyclopentan-4-yl)benzimidazole-5-carboxylate 5.92 g (14.95 mmol) of methyl 3-amino-4-[(2,3-dihydro-7-methoxybenzofuran-2-spiro-1'-cyclopentane-4-carbonyl) amino]benzoate (starting material A2) in 20 ml of thionyl chloride are heated at reflux for 90 min. The reaction mixture is concentrated and co-evaporated repeatedly with toluene. 50 ml of a saturated sodium bicarbonate solution are added, the mixture is extracted with 2×30 ml of dichloromethane and the combined organic phases are dried over magnesium sulphate and concentrated. The product crystallizes from ethyl acetate. This gives 3.54 g of the title compound of m.p. 203° C.

14. Methyl 2-(2,3-dihydro-7-methoxybenzofuran-2-spiro-1'-cyclopentan-4-yl)benzoxazole-5-carboxylate 2.96 g (7.45 mmol) of methyl 3-[(2,3-dihydro-7-methoxybenzofuran-2-spiro-1'-cyclopentane-4-carbonyl)

amino]-4-hydroxybenzoate (starting material A3) in 15 ml of thionyl chloride are heated at reflux for 3 h. The reaction mixture is concentrated and co-evaporated repeatedly with toluene. 50 ml of a saturated sodium bicarbonate solution are added, the mixture is extracted with 2×30 ml of dichloromethane and the combined organic phases are dried over magnesium sulphate and concentrated. The product crystallizes from ethyl acetate. This gives 1.95 g of the title compound of m.p. 167–169° C.

15. Methyl 2-(2,3-dihydro-7-methoxybenzofuran-2-spiro-1'-cyclopentan4-yl)benzoxazol-5-yl-acetate 1.1 g (2.8 mmol) of methyl 3-[(2,3-dihydro-7-methoxybenzofuran-2-spiro-1'-cyclopentane-4-carbonyl)amino]-4-hydroxyphenylacetate (starting material A4; crude product) in 10 ml of thionyl chloride are heated at reflux for 6 h. The reaction mixture is concentrated and co-evaporated repeatedly with toluene. 25 ml of 2 N aqueous sodium hydroxide solution are added, the mixture is extracted with 2×30 ml of dichloromethane and the combined organic phases are dried over magnesium sulphate and concentrated. The product is chromatographed over silica gel [toluene/ethyl acetate=20:1] and crystallized from isopropanol. This gives 200 mg of the title compound of m.p. 130–131° C.

16. Methyl 2-(2,3-dihydro-7-methoxybenzofuran-2-spiro-4'-tetrahydropyran-4-yi)benzoxazole-5-carboxylate 2.0 g (4.83 mmol) of methyl 3-[(2,3-dihydro-7-methoxybenzofuran-2-spiro-4'-tetrahydropyran-4-carbonyl)amino]-4-hydroxybenzoate (starting material A6) in 15 ml of thionyl chloride are heated at 75° C. for 3 h. The reaction mixture is concentrated and co-evaporated repeatedly with toluene. The crude product is recrystallized from acetonitrile. This gives 1.16 g of the title compound of m.p. 180–181° C.

17. Methyl 2-(2,3-dihydro-7-methoxybenzofuran-2-spiro-1'-cyclopentan-4-yl)benzoxazole-6-carboxylate 750 mg (1.9 mmol) of methyl 4-[(2,3-dihydro-7-methoxybenzofuran-2-spiro-1'-cyclopentane-4-carbonyl)amino]-3-hydroxybenzoate (starting material A7) in 4 ml of thionyl chloride are heated at reflux for 6 h. The reaction mixture is concentrated and co-evaporated repeatedly with toluene. 10 ml of 2 N NaOH are added, the mixture is extracted with 2×30 ml of dichloromethane and the combined organic phases are washed with 10 ml of water and then with 10 ml of saturated sodium chloride solution, dried over magnesium sulphate and concentrated. The product crystallizes from ethyl acetate. This gives 170 mg of the title compound of m.p. 178° C.

18. Methyl 2-(2,3-dihydro-7-methoxybenzofuran-2-spiro-4'-tetrahydropyran-4-yi)benzoxazole-6-carboxylate 2.0 g (4.83 mmol) of methyl 4-[(2,3-dihydro-7-methoxybenzofuran-2-spiro-4'-tetrahydropyran-4-carbonyl)amino]-3-hydroxybenzoate (starting material A9) in 15 ml of thionyl chloride are heated at 75° C. for 4.5 h. The reaction mixture is concentrated and co-evaporated repeatedly with toluene. The crude product is recrystallized in acetonitrile. This gives 1.36 g of the title compound of m.p. 215–225° C.

Starting Materials:

A1. 2-[2-(2,3-Dihydro-7-methoxybenzofuran-2-spiro-1'-cyclopentan-4-yl)benzoxazol-5-yl]-propionitrile 800 mg (2.0 mmol) of 2-{3-[(2,3-dihydro-7-methoxybenzofuran-2-spiro-1'-cyclopentane-4-carbonyl)amino]-4-hydroxyphenyl}propionitrile (starting material A5) in 10 ml of thionyl chloride are heated at reflux for 1 h. The reaction mixture is concentrated and co-evaporated repeatedly with toluene. The residue is chromatographed over silica gel [toluene] and the product is crystallized from 5 ml of methanol. This gives 330 mg of the title compound of m.p. 129–132° C.

A2. Methyl 3-amino-4-[(2,3-dihydro-7-methoxybenzofuran-2-spiro-1'-cyclopentane4-carbonyl)amino]benzoate 4.6 g(18.5 mmol) of 2,3-dihydro-7-methoxybenzofuran-2-spiro-1-cyclopentane-4-carboxylic acid (starting material A10) in 10 ml of thionyl chloride are heated at reflux for 45 min. The mixture is then concentrated and co-evaporated repeatedly with toluene. The acyl chloride is dissolved in 50 ml of dioxane and, at 40° C., added dropwise to a solution of 4.3 g(25.9 mmol) of methyl 3,4-diaminobenzoate and 3.6 ml (25.9 mmol) of triethylamine in 100 ml of pyridine. The reaction mixture is heated at 60° C. After the reaction has ended (PLC control), the mixture is concentrated and co-evaporated repeatedly with toluene. The residue is partitioned between water and ethyl acetate. The product crystallizes from toluene. This gives 4.74 g of the title compound.

A3. Methyl 3-[(2,3-dihydro-7-methoxybenzofuran-2-spiro-1'-cyclopentane-4-carbonyl)amino]-4-hydroxybenzoate 1.5 g (6.1 mmol) of 2,3-dihydro-7-methoxybenzofuran-2-spiro-1'-cyclopentane-4-carboxylic acid (starting material A10) in 5 ml of thionyl chloride are heated at reflux for 45 min. The mixture is then concentrated and co-evaporated repeatedly with toluene. The acyl chloride is dissolved in 40 ml of pyridine and the solution is admixed with 1.16 g (6.96 mmol) of methyl 3-amino-4-hydroxybenzoate. The mixture is stirred at RT overnight and heated at 70° C. for a further 5 h. After the reaction has ended, the mixture is concentrated and co-evaporated repeatedly with toluene. The residue is chromatographed over silica gel (toluene/ethyl acetate=9:1). The product crystallizes from methanol. This gives 820 mg of the title compound.

A4. Methyl 3-[(2,3-dihydro-7-methoxybenzofuran-2-spiro-1'-cyclopentane-4-carbonyl)aminol]-4-hydroxyphenylacetate 690 mg (2.8 mmol) of 2,3-dihydro-7-methoxybenzofuran-2-spiro-1'-cyclopentane-4-carboxylic acid (starting material A10) in 5 ml of thionyl chloride are heated at reflux for 60 min. The mixture is then concentrated and co-evaporated repeatedly with toluene. The acyl chloride is dissolved in 20 ml of pyridine and the solution is admixed with 540 mg (2.64 mmol) of methyl 3-amino-4-hydroxyphenylacetate (starting material A12). The mixture is stirred at RT overnight. After the reaction has ended, the mixture is concentrated and co-evaporated repeatedly with toluene. The residue is partitioned between water and ethyl acetate and the organic phase is dried over magnesium sulphate. The crude product is reacted without further purification.

A5. 2-{3-[(2,3-Dihydro-7-methoxybenzofuran-2-spiro-1'-cyclopentane-4-carbonyl)aminol]4-hydroxyphenyl}propionitrile 985 mg (4.0 mmol) of 2,3-dihydro-7-methoxybenzofuran-2-spiro-1'-cyclopentane-4-carboxylic acid (starting material A10) in 5 ml of thionyl chloride are heated at reflux for 2 h. The mixture is then concentrated and co-evaporated repeatedly with toluene. The acyl chloride is dissolved in 5 ml of dioxane and, at RT, added dropwise to a solution of 650 mg (4.0 mmol) of 2-(3-amino-4-hydroxyphenyl)propionitrile (starting material A13) and 0.34 ml (4.2 mmol) of pyridine in 5 ml of dioxane. After 3 h of stirring at RT, the mixture is concentrated and the product is crystallized from 5 ml of methanol. This gives 1.18 g of the title compound of m.p. 151–153° C.

A6. Methyl 3-[(2,3-dihydro-7-methoxybenzofuran-2-spiro-4'-tetrahydropyran-4-carbonyl)-amino]-4-hydroxybenzoate 2.22 g (8.4 mmol) of 2,3-dihydro-7-methoxybenzofuran-2-spiro-4'-tetrahydropyran-4-carboxylic acid (starting material A11) in 10 ml of thionyl chloride are heated at reflux for 75 min. The reaction mixture is then concentrated and co-evaporated repeatedly with toluene. The acyl chloride is dissolved in 40 ml of dioxane and, at 10° C., added dropwise to a solution of 1.4 g (8.4 mmol) of methyl 3-amino-4-hydroxybenzoate and 0.68 ml (8.4 mmol) of pyridine in 20 ml of dioxane. The mixture is stirred at RT for 90 min and then concentrated, and the product is crystallized from 100 ml of methanol. This gives 2.6 g of the title compound of m.p. 258–260° C.

A7. Methyl 4-[(2,3-dihydro-7-methoxybenzofuran-2-spiro-1'-cyclopentane-4-carbonyl)amino]-3-hydroxybenzoate 4.0 g (16.1 mmol) of 2,3-dihydro-7-methoxybenzofuran-2-spiro-1'-cyclopentane-4-carboxylic acid (starting material A10) in 10 ml of thionyl chloride are heated at reflux for 60 min. The reaction mixture is then concentrated and co-evaporated repeatedly with toluene. The acyl chloride is dissolved in 80 ml of pyridine and the solution is admixed with 3.1 g (18.6 mmol) of methyl 4-amino-3-hydroxybenzoate. The mixture is stirred at RT for 4 h and heated at 70° C. for a further 5 h. After the reaction has ended, the mixture is concentrated and co-evaporated repeatedly with toluene. The residue is partitioned between water and ethyl acetate and the organic phase is dried over magnesium sulphate. The product crystallizes when the solvent is evaporated, giving 2.96 g of the title compound of m.p. >230° C.

A8. Ethyl 2-{4-[(2,3-dihydro-7-methoxybenzofuran-2-spiro-1'-cyclopentane-4-carbonyl)amino]-3-hydroxyphenyl}propionate 2.48 g (10.0 mmol) of 2,3-dihydro-7-methoxybenzofuran-2-spiro-1'-cyclopentane-4-carboxylic acid (starting material A10) in 5 ml of thionyl chloride are heated at reflux for 1 h. The reaction mixture is then concentrated and co-evaporated repeatedly with toluene. The acyl chloride is dissolved in 20 ml of dioxane and, at <20° C., added dropwise to a solution of 2.1 g (10.0 mmol) of ethyl 2-(4-amino-3-hydroxyphenyl)propionate (starting material A14) and 1.2 ml (15.0 mmol) of pyridine in 20 ml of dioxane. The mixture is stirred at RT for 2 days. After the reaction has ended, the mixture is concentrated and co-evaporated repeatedly with toluene. The residue is chromatographed over silica gel [toluene/ethyl acetate=4:1]. The product is crystallized from 20 ml of methanol. This gives 3.1 g of the title compound of m.p. 170–172° C.

A9. Methyl 4-[(2,3-dihydro-7-methoxybenzofuran-2-spiro-4'-tetrahydropyran-4-carbonyl)-amino]-3-hydroxybenzoate 2.34 g (9.0 mmol) of 2,3-dihydro-7-methoxybenzofuran-2-spiro-4'-tetrahydropyran-4-carboxylic acid (starting material A11) in 10 ml of thionyl chloride are heated at reflux for 75 min. The reaction mixture is then concentrated and co-evaporated repeatedly with toluene. The acyl chloride is dissolved in 40 ml of dioxane and, at 10° C., added dropwise to a solution of 1.51 g (9.0 mmol) of methyl 4-amino-3-hydroxybenzoate and 0.73 ml (9.0 mmol) of pyridine in 80 ml of dioxane. The mixture is stirred at RT for 90 min and then concentrated, and the product is triturated with 100 ml of hot methanol. This gives 3.27 g of the title compound of m.p.>260° C.

A10. 2,3-Dihydro-7-methoxybenzofuran-2-spiro-1'-cyclopentane4-carboxylic acid

The preparation of the title compound is described in WO96l03399.

A11. 2,3-Dihydro-7-methoxybenzofuran-2-spiro-4'-tetrahydropyran-4-arboxylic acid The preparation of the title compound is described in WO96/03399.

A12. Methyl 3-amino-4-hydroxyphenylacetate

Lit.: D. R. Shridhar et.al.; Indian J. Chem. Sect. B; 20 (1981) 311–313

A13. 2-(3-Amino-4-hydroxyphenyl)propionitrile

Lit.: D. W. Dunwell, D. Evans, T. A. Hicks; J. Med. Chem. 18 (1975) 53–58

A14. Ethyl 2-(4-amino-3-hydroxyphenyl)propionate

Lit.: D. W. Dunwell, D. Evans; J. Med. Chem. 20 (1977) 797–801

Commercial Applicability

The compounds according to the invention have valuable pharmacological properties which make them commercially utilizable. As selective cyclic nucleotide phosphodiesterase (PDE) inhibitors (namely of type 4), they are suitable on the one hand as bronchial therapeutics (for the treatment of airway obstructions on account of their dilating but also on account of their respiratory rate- or respiratory drive-increasing action) and for the elimination of erectile dysfunction on account of the vasodilating action, but on the other hand especially for the treatment of disorders, in particular of inflammatory nature, e.g. of the airways (asthma prophylaxis), of the skin, of the central nervous system, of the intestine, of the eyes and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumour necrosis factor (TNF) or oxygen radicals and proteases. The compounds according to the invention are distinguished here by low toxicity, good enteral absorption (high bioavailability), a large therapeutic breadth and the absence of significant side-effects.

On account of their PDE-inhibiting properties, the compounds according to the invention can be employed in human and veterinary medicine and therapeutics, where they can be used, for example, for the treatment and prophylaxis of the following illnesses: acute and chronic (in particular inflammatory and allergen-induced) airway disorders of various origins (bronchitis, allergic bronchitis, bronchial asthma, emphysema, COPD); dermatoses (especially of proliferative, inflammatory and allergic type) such as, for example, psoriasis (vulgaris), toxic and allergic contact eczema, atopic eczema, seborrhoeic eczema, lichen simplex, sunburn, pruritus in the anogenital area, alopecia areata, hypertrophic scars, discoid lupus erythematosus, follicular and wide-area pyodermias, endogenous and exogenous acne, acne rosacea and other proliferative, inflammatory and allergic skin disorders; disorders which are based on an excessive release of TNF and leukotrienes, e.g. disorders of the arthritis type (rheumatoid arthritis, rheumatoid spondylitis, osteoarthritis and other arthritic conditions), disorders of the immune system (AIDS, multiple sclerosis), graft-versus-host reactions, transplant rejection reactions, symptoms of shock [septic shock, endotoxin shock, gram-negative sepsis, toxic shock syndrome and ARDS (adult respiratory distress syndrome)], and generalized inflammations in the gastrointestinal area (Crohn's disease and ulcerative colitis); disorders which are based on allergic and/or chronic, faulty immunological reactions in the area of the upper airways (pharynx, nose) and the adjacent regions (paranasal sinuses, eyes), such as, for example, allergic rhinitis/sinusitis, chronic rhinitis/sinusitis, allergic conjunctivitis and nasal polyps; but also disorders of the heart which can be treated by PDE inhibitors, such as, for example, cardiac insufficiency, or disorders which can be treated on account of the tissue-relaxant action of the PDE inhibitors, such as, for example, erectile dysfunction or colics of the kidneys and the ureters in connection with kidney stones. In addition, the compounds according to the invention can be employed for the treatment of diabetes insipidus and disorders in connection with disturbances of brain metabolism, such as, for example, cerebral senility, senile dementia (Alzheimer's dementia), multiinfarct dementia or alternatively disorders of the CNS, such as, for example, depressions or arteriosclerotic dementia.

A further subject of the invention is a process for the treatment of mammals, including humans, which are suffering from one of the abovementioned illnesses. The process is characterized in that a therapeutically efficacious and pharmacologically tolerable amount of one or more of the compounds according to the invention is administered to the sick mammal.

The invention further relates to the compounds according to the invention for use in the treatment and/or prophylaxis of illnesses, in particular the illnesses mentioned.

The invention likewise relates to the use of the compounds according to the invention for the production of medicaments which are employed for the treatment and/or prophylaxis of the illnesses mentioned.

Medicaments for the treatment and/or prophylaxis of the illnesses mentioned, which contain one or more of the compounds according to the invention, are furthermore a subject of the invention.

A further subject of the invention is a commercial product, consisting of a customary secondary pack, a primary pack containing the medicament (for example an ampoule or a blister pack) and, if desired, an information leaflet, the medicament exhibiting antagonistic action against cyclic nucleotide phosphodiesterases of type 4 (PDE4) and leading to the attenuation of the symptoms of illnesses which are connected with cyclic nucleotide phosphodiesterases of type 4, and the suitability of the medicament for the prophylaxis or treatment of illnesses which are connected with cyclic nucleotide phosphodiesterases of type 4 being indicated on the secondary pack or on the information leaflet of the commercial product, and the medicament containing one or more compounds of the formula I according to the invention. The secondary pack, the primary pack containing the medicament and the information leaflet otherwise comply with what would be regarded as standard to the person skilled in the art for medicaments of this type.

The medicaments are prepared by processes which are known per se and familiar to the person skilled in the art. As medicaments, the compounds according to the invention (=active compounds) are either employed as such, or preferably in combination with suitable pharmaceutical excipients, e.g. in the form of tablets, coated tablets, capsules, suppositories, patches, emulsions, suspensions, gels or solutions, the active compound content advantageously being between 0.1 and 95%.

The person skilled in the art is familiar on the basis of his/her expert knowledge with the excipients which are suitable for the desired pharmaceutical formulations. In addition to solvents, gel-forming agents, ointment bases and other active compound vehicles, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this, these are either administered directly as a powder (preferably in micronized form) or by nebulization of solutions or suspensions which contain them. With respect to the preparations and administration forms, reference is made, for example, to the details in European Patent 163 965.

For the treatment of dermatoses, the compounds according to the invention are in particular used in the form of those medicaments which are suitable for topical application. For the production of the medicaments, the compounds according to the invention (=active compounds) are preferably mixed with suitable pharmaceutical excipients and further processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by methods known per se. Dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.1 and 3 mg per day. The customary dose in the case of systemic therapy (p.o. or i.v.) is between 0.03 and 3 mg per kilogram per day.

Biological Investigations

In the investigation of PDE4 inhibition at the cellular level, the activation of inflammatory cells has particular importance. As an example, the FMLP (N-formyl-methionyl-leucyl-phenylalanine)-induced superoxide production of neutrophilic granulocytes may be mentioned, which can be measured as luminol-potentiated chemoluminescence [McPhail LC, Strum SL, Leone PA and Sozzani S, The neutrophil respiratory burst mechanism. In "Immunology Series" 1992, 57, 47–76; ed. Coffey RG (Marcel Decker, Inc. New York-Basle-Hong Kong)].

Substances which inhibit chemoluminescence and cytokine secretion and the secretion of inflammatory mediators on inflammatory cells, in particular neutrophilic and eosinophilic granulocytes, T lymphocytes, monocytes and macrophages, are those which inhibit PDE4. This isoenzyme of the phosphodiesterase families is particularly represented in granulocytes. Its inhibition leads to an increase in the intracellular cyclic AMP concentration and thus to the inhibition of cell activation. PDE4 inhibition by the substances according to the invention is thus a central indicator of the suppression of inflammatory processes (Giembycz MA, Could isoenzyme-selective phosphodiesterase inhibitors render bronchodilatory therapy redundant in the treatment of bronchial asthma?. Biochem Pharmacol 1992, 43, 2041–2051; Torphy TJ et al., Phosphodiesterase inhibitors: new opportunities for treatment of asthma. Thorax 1991, 46, 512–523; Schudt C et al., Zardaverine: a cyclic AMP PDE 3/4 inhibitor. In "New Drugs for Asthma Therapy", 379–402, Birkhäuser Verlag Basle 1991; Schudt C et al., Influence of selective phosphodiesterase inhibitors on human neutrophil functions and levels of cAMP and Ca; Naunyn-Schmiedebergs Arch Pharmacol 1991, 344, 682–690; Tenor H and Schudt C, Analysis of PDE isoenzyme profiles in cells and tissues by pharmacological methods. In "Phosphodiesterase Inhibitors", 21–40, "The Handbook of Immunopharmacology", Academic Press, 1996; Hatzelmann A et al., Enzymatic and functional aspects of dual-selective PDE3/4-inhibitors. In "Phosphodiesterase Inhibitors", 147–160. "The Handbook of Immunopharmacology", Academic Press, 1996).

Inhibition of PDE4 Activity

Methodology

The activity test was carried out according to the method of Bauer and Schwabe, which was adapted to microtitre plates (Naunyn-Schmiedeberg's Arch. Pharmacol. 1980, 311, 193–198). The PDE reaction takes place in the first step here. In a second step, the resulting 5'-nucleotide is cleaved by a 5'-nucloetidase of the snake venom of Crotalus atrox to the uncharged nucleoside. In the third step, the nucleoside is separated from the remaining charged substrate on ion-exchange columns. The columns are eluted directly into minivials, into which 2 ml of scintillator fluid are additionally added, for counting using 2 ml of 30 mM ammonium formate (pH 6.0).

The inhibitory values determined for the compounds according to the invention [inhibitory concentration as -log $IC_{50}$ (mol/l)] follow from the following Table A, in which the numbers of the compounds correspond to the numbers of the examples.

TABLE A

Inhibition of the PDE4 Activity

| compound | -log $IC_{50}$ |
|---|---|
| 1 | 7.87 |
| 2 | 7.69 |
| 3 | 7.65 |
| 6 | 7.05 |
| 7 | 6.80 |
| 8 | 8.21 |
| 9 | 6.90 |
| 11 | 6.85 |
| 12 | 6.42 |

What is claimed is:
1. A compound of the formula I

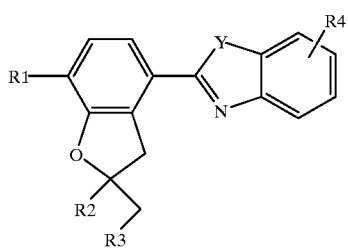

(I)

in which
Y is O (oxygen) or NH,
R1 is 1–4C-alkoxy, 3–7C-cycloalkoxy, 3–7C-cycloalkylmethoxy, benzyloxy or completely or predominantly fluorine-substituted 1–4C-alkoxy,
R2 is hydrogen or 1–4C-alkyl and
R3 is hydrogen or 1–4C-alkyl,
or in which
R2 and R3, together and including the two carbon atoms to which they are attached, are a spiro-linked 5-, 6- or 7-membered hydrocarbon ring which, if desired, is interrupted by an oxygen atom,
R4 is C(O)R5, C(O)R6, —$C_nH_{2n}$—C(O)R5 or —$C_nH_{2n}$—C(O)R6, where R5 is hydroxyl, 1–7C-alkoxy, 3–7C-cycloalkoxy, 3–7C-cycloalkylmethoxy, $H_2N$—$C_mH_{2m}$—O— or R51 (R52)N—$C_pH_{2p}$—O—, where
R51 is hydrogen, 1–7C-alkyl, 3–7C-cycloalkyl or 3–7C-cycloalkylmethyl and
R52 is 1–7C-alkyl, 3–7C-cycloalkyl or 3–7C-cycloalkylmethyl, or where
R51 and R52, together and including the nitrogen atom to which both are attached, are a 5-, 6- or 7-membered hydrocarbon ring which, if desired, is additionally interrupted by a group —N(R7)— or an oxygen atom,
R6 is N(R61)R62, where R61 and R62 independently of one another are hydrogen, 1–7C-alkyl, 3–7C-cycloalkyl or 3–7C-cycloalkylmethyl,
R7 is hydrogen or 1–4C-alkyl,
m is 2,3 or 4,
n is 1,2,3 or 4,
p is 1,2,3 or 4,
and the salts of these compounds.
2. A compound of formula I according to claim 1 in which
Y is O (oxygen) or NH,
R1 is 1–4C-alkoxy, 3–5C-cycloalkoxy, 3–5C-cycloalkylmethoxy, or completely or predominantly fluorine-substituted 1–2C-alkoxy,
R2 is 1–4C-alkyl and
R3 is hydrogen or 1–4C-alkyl,
or in which
R2 and R3, together and including the two carbon atoms to which they are attached, are a spiro-linked cyclopentane, cyclohexane, tetrahydrofuran or tetrahydropyran ring,
R4 is C(O)R5, C(O)R6, —$C_nH_{2n}$—C(O)R5 or —$C_nH_{2n}$—C(O)R6, where R5 is hydroxyl, 1–7C-alkoxy, 3–7C-cycloalkoxy, 3–7C-cycloalkylmethoxy, $H_2N$—$C_mH_{2m}$—O— or R51 (R52)N—$C_pH_{2p}$—O—, where
R51 is hydrogen or 1–4C-alkyl and
R52 is 1–4C-alkyl, or where
R51 and R52, together and including the nitrogen atom to which both are attached, are a 5-, 6- or 7-membered hydrocarbon ring which, if desired, is additionally interrupted by a group —N(R7)— or an oxygen atom,
R6 is N(R61)R62, where R61 and R62 independently of one another are hydrogen or 1–4C-alkyl,
R7 is hydrogen or 1–4C-alkyl,
m is 2,3 or 4,
n is 1 or 2,
p is 1,2,3 or 4,
and the salts of these compounds.
3. A compound of formula I according to claim 1 in which
Y is O (oxygen) or NH,
R1 is methoxy, ethoxy, cyclopropylmethoxy or completely or predominantly fluorine-substituted 1–2C-alkoxy,
R2 and R3, together and including the two carbon atoms to which they are attached, are a spiro-linked cyclopentane, cyclohexane, tetrahydrofuran or tetrahydropyran ring,
R4 is C(O)R5, C(O)R6, —$C_nH_{2n}$—C(O)R5 or —$C_nH_{2n}$—C(O)R6, where
R5 is hydroxyl, 1–4C-alkoxy or R51 (R52)N—$C_pH_{2p}$—O—, where
R51 is hydrogen or 1–4C-alkyl and R52 is 1–4C-alkyl, or where R51 and R52, together and including the nitrogen atom to which both are attached, are a 6-membered hydrocarbon ring which, if desired, is interrupted by a group —N(R7)— or an oxygen atom, R6 is N(R61)R62, where R61 and R62 independently of one another are hydrogen or 1–4C-alkyl, R7 is hydrogen or 1–4C-alkyl, n is 1 or 2, p is 1,2,3or 4, and the salts of these compounds.

4. A compound of formula I according to claim 1 in which

Y is O (oxygen) or NH,

R1 is methoxy,

R2 and R3, together and including the two carbon atoms to which they are attached, are a spiro-linked cyclopentane or tetrahydropyran ring, R4 is carboxyl, carboxymethyl, carboxymethylmethyl, methoxycarbonylmethyl, methoxycarbonylmethylmethyl, methoxycarbonyl, aminocarbonyl or morpholin-4-ylethyleneoxycarbonyl, and the salts of these compounds.

5. A compound of formula I according to claim 1 in which

Y is O(oxygen) or NH,

R1 is methoxy,

R2 and R3, together and including the two carbon atoms to which they are attached, are a spiro-linked cyclopentane ring, R4 is carboxyl, carboxymethyl, carboxymethylmethyl, methoxycarbonylmethyl, methoxycarbonylmethylmethyl, methoxycarbonyl, aminocarbonyl or morpholin-4-ylethyleneoxycarbonyl, and the salts of these compounds.

6. A pharmaceutical composition comprising a compound according to claim 1 or a pharmaceutically acceptable salt thereof together with a usual pharmaceutical auxiliary and/or carrier.

7. A method of treating an acute or chronic airway disorder, a dermatosis, a disorder based on excessive release of TNF or leikotriene, a disorder of the immune system, a graph-versus-host reaction, a transplant rejection reaction, a symptom of shock, a generalized inflammation in the intestinal area, a disorder based on allergic, and/or chronic, faulty immunological reaction in the upper airway or adjacent region, a heart disorder which can be treated by a PDE inhibitor, diabetes insipidus, a disorder in connection with a disturbance of brain metabolism, or a disorder of the CNS, which method comprises administering an effective amount of a selective cyclic nucleotide phosphodiesterase (PDE) inhibitor wherein the PDE inhibitor is a compound according to claim 1 or a pharmacologically acceptable salt thereof.

8. A method of treating an airway disorder amenable to treatment with a PDE inhibitor, which comprises administering an effective amount of a compound according to claim 1, or a pharmacologically acceptable salt thereof, to a subject afflicted with such disorder.

9. A method of compounding a pharmaceutical composition for treating a dermatosis amenable to treatment with a PDE inhibitor, which comprises combining a compound according to claim 1, or a pharmacologically acceptable salt thereof, with a pharmaceutical auxiliary and/or carrier.

* * * * *